United States Patent
Ismaili et al.

(10) Patent No.: US 7,217,840 B2
(45) Date of Patent: May 15, 2007

(54) METHOD FOR PREPARING 1,3,5-TRIAMINOBENZENE AND HYDROLYZING IT INTO HIGH-PURITY PHLOROGLUCINAL

(75) Inventors: Lhassane Ismaili, Besancon (FR); Bernard Refouvelet, Besancon (FR); Alain Xicluna, Annoire (FR)

(73) Assignee: PHV Analytic, Lons le Saunier (FR)

( * ) Notice: Subject to any disclaimer, the term of this patent is extended or adjusted under 35 U.S.C. 154(b) by 334 days.

(21) Appl. No.: 10/517,716

(22) PCT Filed: Jun. 6, 2003

(86) PCT No.: PCT/FR03/01703

§ 371 (c)(1), (2), (4) Date: Dec. 10, 2004

(87) PCT Pub. No.: WO03/104194

PCT Pub. Date: Dec. 18, 2003

(65) Prior Publication Data

US 2005/0165256 A1    Jul. 28, 2005

(30) Foreign Application Priority Data

Jun. 11, 2002  (FR) .................................. 02 07177

(51) Int. Cl.
*C07C 209/10* (2006.01)
*C07C 37/05* (2006.01)
(52) U.S. Cl. ...................... 564/405; 568/767
(58) Field of Classification Search ................ 564/405; 568/767
See application file for complete search history.

(56) References Cited

U.S. PATENT DOCUMENTS

| | | | |
|---|---|---|---|
| 2,461,498 A | 2/1949 | Krueger | |
| 2,773,908 A | 12/1956 | Cake et al. | |
| 3,028,410 A | 4/1962 | Zimmer et al. | |
| 3,230,266 A * | 1/1966 | Baldoni et al. | 568/767 |
| 3,678,114 A | 7/1972 | Miller et al. | |
| 3,904,695 A | 9/1975 | Hendrickx et al. | |
| 3,959,388 A | 5/1976 | De Heij et al. | |
| 4,057,588 A | 11/1977 | Zengel et al. | |
| 4,071,555 A | 1/1978 | Zengel et al. | |
| 4,115,451 A | 9/1978 | Zengel et al. | |
| 4,157,450 A | 6/1979 | Zengel et al. | |
| 4,296,260 A | 10/1981 | Zielke et al. | |
| 4,380,670 A * | 4/1983 | Nishiyama et al. | 564/407 |
| 4,751,332 A | 6/1988 | Prescher et al. | |
| 4,751,333 A | 6/1988 | Prescher et al. | |
| 5,510,533 A * | 4/1996 | Kobayashi et al. | 564/407 |

FOREIGN PATENT DOCUMENTS

| | | |
|---|---|---|
| DE | 102 358 | 12/1897 |
| DE | 1195327 | 6/1965 |
| EP | 0 016 481 | 5/1983 |
| EP | 0 236 785 | 5/1989 |
| EP | 0 241 664 | 8/1989 |
| FR | 1289647 | 2/1962 |
| GB | 693 752 | 7/1953 |
| GB | 1106088 | 3/1968 |
| GB | 1022733 | 3/1996 |
| WO | WO-00/56911 | 9/2000 |

OTHER PUBLICATIONS

HT Clarke and W. Hartman, "Phloroglucinol", *Organic Synthesis*, vol. 45., pp. 444-446, 1932.
*Organic Synthesis*, "Phloroglucinol," vol. 45, pp. 74-76, Oct. 30, 2001.
P.M. Heertjes, *Laboratory of Chemical Technology of the Technical University*, "Phloroglucinol From Picryl Chloride," pp. 452-459, Mar. 5, 1959.
Paul Hepp, "Ueber Trinitroderivate des Benzols und Toluols," pp. 344-380, Nov. 11, 1882.
H. Weidel and J. Pollak, "Zur Kenntniss der Nitrosoderivate der Phloro-glucinather," pp. 15-17 and 22-35, Publication Ann. 1900, Nov. 8, 1889.

* cited by examiner

*Primary Examiner*—Peter O'Sullivan
(74) *Attorney, Agent, or Firm*—Marshall Gerstein & Borun LLP

(57) ABSTRACT

The invention concerns a method for method for preparing 1,3,5-triaminobenzene, characterized in that it comprises a step which consists in amination of a compound of formula (I), wherein: A represents a halogen atom or a $NH_2$ group; $X_1$ and $X_2$, identical or different, represent each a halogen atom, the amination step being carried out in the presence of ammonia and a catalyst selected from the group consisting of copper salts, cupric and cuprous oxides or mixtures thereof at a temperature ranging between 150° C. and 250° C. and at a pressure higher that 35 bars

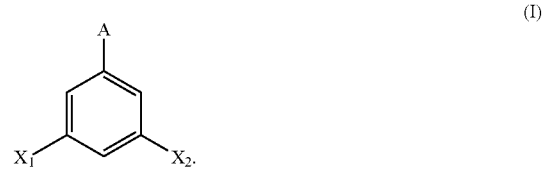

(I)

28 Claims, No Drawings

METHOD FOR PREPARING 1,3,5-TRIAMINOBENZENE AND HYDROLYZING IT INTO HIGH-PURITY PHLOROGLUCINAL

The present invention relates to a method of preparing 1,3,5-triaminobenzene and its hydrolysis and subsequent purification to high-purity phloroglucinol.

Phloroglucinol is a compound known both to the colorist and to the pharmacist. Phloroglucinol initially attracted interest for its use in dyeing for papers or textiles. It was only later that pharmacists uncovered its musculotropic antispasmolytic properties. It is clear, however, that the purity requirements are much higher when phloroglucinol is used as an antispasmodic than as a dyeing agent.

The literature extensively describes the preparation of phloroglucinol by hydrolysis of 1,3,5-triaminobenzene in the presence of concentrated hydrochloric acid. 1,3,5-Triaminobenzene therefore represents a very widely used intermediate in the preparation of phloroglucinol.

As far as the preparation of 1,3,5-triaminobenzene is concerned, a large number of synthesis routes have already been proposed.

Among the synthesis routes already proposed, mention may be made of U.S. Pat. No. 4,380,670. That patent describes the preparation of 1,3,5-triaminobenzene from 3,5-diaminochlorobenzene in the presence of ammonia and of salts or oxides of copper in various oxidation states at a temperature of between 150 and 250° C. That patent specifies, moreover, in column 1, lines 38 to 42, that the preparation of 1,3,5-triaminobenzene by direct amination of 1,3,5-trichlorobenzene is not possible. The authors of the patent clearly indicate that the desired amination reaction does not take place.

Another possible synthesis route for 1,3,5-triaminobenzene is described by H. T. Clarke and W. W. Hartman in the article entitled "Phloroglucinol", organic synthesis, vol. 45. In that article, 1,3,5-triaminobenzene is obtained starting from 2,4,6-trinitrobenzoic acid in concentrated hydrochloric acid in the presence of tin. However, the synthesis of trinitrobenzoic acid is relatively lengthy and awkward, necessitating the preparation of trinitrotoluene (TNT), which is explosive. Moreover, the preparation of 1,3,5-triaminobenzene starting from trinitrobenzoic acid gives rise to difficulties of purification. This is because, following hydrolysis of 1,3,5-triaminobenzene, it is particularly difficult to purify the resulting phloroglucinol. Consequently, a high-purity phloroglucinol meeting pharmaceutical requirements cannot be obtained by that route.

As regards, more specifically, the subsequent step of hydrolysis of 1,3,5-triaminobenzene to give phloroglucinol, mention may be made of U.S. Pat. No. 4,115,451. That patent recommends hydrolysis of 1,3,5-triaminobenzene in an excess of concentrated hydrochloric acid at a temperature of 100 to 200° C., to end up with phloroglucinol. This hydrolysis step is followed by a step of extraction with an acetic ester. The extracted phase containing the phloroglucinol crystallizes after cooling. After filtration, the phloroglucinol is recrystallized from water containing active carbon.

In spite of all this literature relating to the synthesis of 1,3,5-triaminobenzene and relating to the hydrolysis to phloroglucinol, the preparation of a high-purity phloroglucinol still poses numerous problems to the industrialists of the pharmaceutical sector. The purity requirements imposed by the pharmacopeia call for a method of synthesis which yields a phloroglucinol which is in accordance with the criteria of pharmaceutical purity.

On the other hand, improving the synthesis routes, in particular the cost price of the raw materials, and reducing the number of synthesis steps have favorable consequences for the manufacturing costs of a pharmaceutical active principle.

It is while working in this direction that the inventors have succeeded in developing a method of preparing 1,3,5-triaminobenzene and then hydrolyzing it to phloroglucinol, which is original, effective and less costly. This method also makes it possible to obtain a high-purity phloroglucinol which is entirely in accordance with pharmaceutical requirements.

In general, the invention provides a method of preparing 1,3,5-triaminobenzene which comprises a step a) of amination of a compound of formula (I):

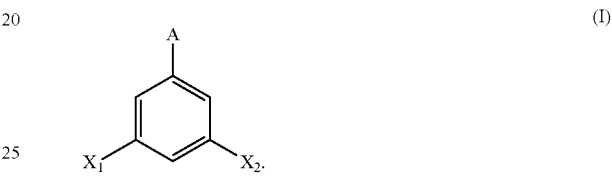

in which:
A represents a halogen atom or an $NH_2$ group,
$X_1$ and $X_2$, which are identical or different, each represent a halogen atom, said amination step being conducted in the presence of ammonia and a catalyst selected from the group consisting of copper salts, cupric and cuprous oxides and mixtures thereof, at a temperature ranging from 150° C. to 250° C. and at a pressure of greater than 35 bars.

It should be noted that the method according to the invention is entirely original in relation to the prior art presented above.

This is because, as described earlier on above, the inventors have gone against a technical prejudice from the U.S. Pat. No. 4,380,670 and have overcome it. The inventors have discovered, against all expectation, that it is possible to carry out the amination of the compound of formula (I), that is, in particular, of 1,3,5-triaminobenzene or of 3,5-dichloroaniline, and to obtain 1,3,5-triaminobenzene quantitatively, in a single step, and starting from compounds which are stable and available commercially.

In formula (I) A represents an $NH_2$ group or a halogen atom, i.e., bromine, chlorine, fluorine or else iodine. Preferably A represents an $NH_2$ group, bromine or chlorine, and more preferably chlorine.

$X_1$ and $X_2$ are identical or different from one another and represent a halogen atom, i.e., as indicated above, bromine, chlorine, fluorine or else iodine, preferably chlorine or bromine.

Advantageously $X_1$ and $X_2$ are identical and each represent a bromine or chlorine atom, preferably a chlorine atom.

The preferred compounds (I) are 1,3,5-triaminobenzene, 3,5-dichloroaniline, 1,3,5-tribromobenzene or 3,5-dibromoaniline.

As far as the catalyst is concerned it is preferably selected from the group consisting of halogen salts of copper, also called copper halides, and more preferably from copper bromide, copper chloride, copper iodide and mixtures thereof.

This catalyst is preferably used in amounts ranging from 1% to 5%, this percentage expressing the total weight of catalyst, based on the total weight of reactant.

Moreover, this step a) is conducted in the presence of an ammonia solution whose concentration is preferably from 20% to 30%, and more preferably whose concentration is 28%.

In the process according to the invention, this ammonia solution is used in an amount ranging preferably from 70% to 95% by weight, based on the total weight of the reactants.

The process according to the invention may further comprise an additional step of hydrolysis of the 1,3,5-triaminobenzene to phloroglucinol, and also possible steps of purification of the latter compound.

The process according to the invention provides, moreover, a 1,3,5-triaminobenzene which is particularly appropriate for use for preparing phloroglucinol by hydrolysis.

This hydrolysis may thus be carried out as follows:

b) hydrolysis of the 1,3,5-triaminobenzene obtained in step a) in the presence of hydrochloric acid or of sulfuric acid at a temperature greater than 90° C., and preferably from 100 to 120° C., for a time of 6 to 24 h, to give a hydrolysate containing phloroglucinol, c) optionally filtration at ambient temperature of the hydrolysate obtained in step b), d) extraction of phloroglucinol from the hydrolysate obtained in step b) or from the filtrate obtained in step c), using ethyl ether or another, ester-based solvent, for example, ethyl benzoate, ethyl acetate, isopropyl acetate or n-butyl acetate.

In this hydrolysis step the hydrochloric acid may in particular be at a concentration of 20% to 40%, preferably a concentration of 37%, and in amounts ranging from 10% to 15% by weight, based on the total weight of reactant. The sulfuric acid may be at a concentration of 10% V to 100% V, preferably from 50% V to 98% V, the amounts ranging from 2 to 6 $H^+$ equivalents, preferably 4 $H^+$ equivalents.

It is possible to follow a number of routes for the purification of the phloroglucinol.

One of these routes comprises the following step:

e1) recrystallization of the phloroglucinol obtained in step d) from water containing active carbon, to give a high-purity phloroglucinol.

Another route comprises the succession of the following steps:

e2) concentration of the hydrolysate obtained in step b) or of the phloroglucinol solution obtained in step d) until phloroglucinol precipitates, f2) filtration of the precipitate obtained in step e2), g2) recrystallization of the phloroglucinol obtained in step f2) from water containing active carbon, h2) takeup of the recrystallized phloroglucinol obtained in step g2) in ethyl ether containing active carbon, to give a phloroglucinol solution, i2) evaporation of the phloroglucinol solution obtained in step h2), to give a high-purity phloroglucinol.

In these purification steps, both the active carbon and the solvents are used in amounts which are commonly employed by the skilled worker.

This purification method involves the use of ether and makes it possible to isolate a phloroglucinol which meets the requirements of the pharmacopeia, since it exhibits, among other properties, a coloration less than or equal to BY 5.

Purity control analyses were carried out according to methods described in the present patent application. According to these analyses the phloroglucinol obtained according to the method of the invention contains, in total, less than 0.5% of impurities, preferably less than 0.2% of impurities and more preferably still less than 0.1% of impurities by weight, based on the total weight of phloroglucinol obtained.

The three impurities which are most characteristic and most widely represented in this type of phloroglucinol preparation are 3,5-dichloroaniline, phloroglucide and resorcinol. Measurement has shown that the phloroglucinol obtained according to the method of the invention contains not more than 0.1%, preferably not more than 0.05% and more preferably not more than 0.01% of these three impurities by weight, based on the total weight of phloroglucinol obtained.

Impurity levels of this kind completely satisfy the requirements called for by the French pharmacopeia. Consequently the phloroglucinol obtained by the method according to the invention is entirely indicated for the preparation of a medicinal product, in particular for the treatment of disorders associated with muscular spasms or for the treatment of pain in a mammal.

METHODS USED FOR THE ANALYSES

A—Identification

The phloroglucinol obtained is checked according to the monograph "Phloroglucinol" in the French Pharmacopeia, Xth edition, July 1987.

Infrared spectrum: 3211 $cm^{-1}$, 1624 $cm^{-1}$, 1506 $cm^{-1}$, 1419.5 $cm^{-1}$, 1157.2 $cm^{-1}$, 1008.7 $cm^{-1}$, 813 $cm^{-1}$ $^1H$ NMR spectrum at 300 MHz in DMSOd6: 5.8 ppm (s, 3H, C—H) and 9.1 ppm (s, 3H, O—H).

$^{13}C$ NMR spectrum at 300 MHz in DMSOd6: 95.9 (C—H); 159.6 (C—OH).

B—Purity

The impurities looked for are primarily 3,5-dichloroaniline, phloroglucide, which results from the dimerization of phloroglucinol, and resorcinol.

3,5-Dichloroaniline is present in the phloroglucinol produced when the method according to the invention proceeds via step a). 3,5-Dichloroaniline is in effect one of the reactants of this step. In contrast, phloroglucide and resorcinol are present in phloroglucinol irrespective of its preparation steps.

In practice, high-performance liquid chromatography is used in order to look for these impurities. The methods which can be used are in particular as follows:

1—Identification and Assay of 3,5-dichloroaniline 1.a—Comparative High-performance Liquid Chromatography:

Preparation of Solutions:

Eluent: acetonitrile —$H_3PO_4$ (85%) at 0.5 $g.l^{-1}$ of water;

Control solution ($T_1$): dissolve 20.0 mg of reference 3,5-dichloroaniline in 100 ml of eluent (96% alcohol; acetonitrile, dilute acid);

Type of column: Agilent Interchim ZORBAX SB-CN column (4.6×250 mm) 5 µm, held at 35° C. with detection at 220 nm and a flow rate of 1 $ml.min^{-1}$;

Control solution ($T_2$): dilute control solution ($T_1$) to $1/100$th in water;

Assay solution (E): dissolve 200.0 mg of phloroglucinol to be analyzed in 100 ml of water.

Technique:

The techniques employed may vary slightly depending on the equipment used. By way of example the technique may be as follows:

inject exactly 10 µl of each of the control solutions and assay solution into a suitably equipped and regulated chromatograph.

for each of the solutions measure the areas of the peaks obtained and their attention time. 3,5-Dichloroaniline gives a peak having a retention time RT=6.4 min.

Calculation:

Let:

$A_1$ be the value of the area of the 3,5-dichloroaniline peak obtained for control solution (T2);

$A_2$ be the value of the area of the 3,5-dichloroaniline peak obtained for the assay solution (E).

The % of 3,5-dichloroaniline content will be given by the expression:

$$t=(A_2/A_1)\times 0.1$$

Expression of the Result:

The 3,5-dichloroaniline content of the phloroglucinol must not be greater than 0.1%.

2—Identification and Assay of Phloroglucide 2.a—Comparative High-performance Liquid Chromatography:

column: Agilent Interchim ZORBAX SB-CN (4.6×250 mm) 5 µm, held at 35° C.;

1.5 ml.min$^{-1}$—detection: 220 nm.

Preparation of Solutions:

Eluent: $H_3PO_4$ (85%) at 0.5 g.l$^{-1}$ of water;

Control solution ($T_1$): dissolve 20.0 mg of reference phloroglucide in 100 ml of methanol;

Control solution ($T_2$): dilute control solution ($T_1$) to ¹⁄₁₀₀th in water;

Assay solution (E): dissolve 200 mg of phloroglucinol to be analyzed in 100 ml of water.

Technique:

The techniques employed may vary slightly according to the equipment used. By way of example the technique may be as follows:

inject exactly 10 µl of each of the control solutions and assay solution into a suitably equipped and regulated chromatograph.

for each of the solutions measure the areas of the peaks obtained and their retention time. Phloroglucide gives a peak having a retention time of $T_R$=12.6 min and resorcinol a chromatographic peak of $T_R \approx 7.0$ min.

Calculation:

Let:

$A_1$ be the value of the area of the peak of impurity obtained for the control solution;

$A_2$ be the value of the area of the peak of impurity obtained for the assay solution.

The % phloroglucide content will be given by the expression:

$$t=(A_2/A_1)\times 0.1$$

Expression of the Result:

The phloroglucide content of the phloroglucinol must not be greater than 0.1%.

The invention will now be described in greater detail by means of the examples which follow. The purpose of these examples is to illustrate the method of the invention without limiting it to these simple embodiments.

EXAMPLE 1

Preparation of 1,3,5-triaminobenzene from 1,3,5-trichlorobenzene and its hydrolysis to phloroglucinol A pressurized vessel is charged with 5 g (27.5 mmol) of 1,3,5-trichlorobenzene and 70 ml of 28% aqueous ammonia and 800 mg of copper iodide are added. The mixture is heated at 180° C. and at a pressure of 40 bar for 24 h. After the mixture has cooled, 40 g of crushed ice and 79 ml of concentrated hydrochloric acid are added and then the mixture is heated at 120° C. for 20 h. The contents of the flask are filtered. The filtrate is subsequently extracted with 3×40 ml of ethyl ether. The ethereal phase is subsequently dried and then evaporated to give 1.4 g of phloroglucinol, corresponding to a yield of 40%

EXAMPLE 2

Preparation of 1,3,5-triaminobenzene from 3,5-dichloroaniline and its hydrolysis to phloroglucinol A pressurized vessel is charged with 3 g (18.5 mmol) of 3,5-dichloroaniline and 50 ml of 28% aqueous ammonia and 300 mg of copper iodide are added. The mixture is heated at 180° C. and at a pressure of 40 bar for 24 h. After the mixture has been cooled, 30 g of crushed ice and a concentrated, 37% solution of hydrochloric acid are added to a pH of 1, and then the mixture is heated at 120° C. for 20 h.

The contents of the flask are filtered. The filtrate is subsequently extracted with 3×40 ml of ethyl ether, dried and then evaporated. This gives a phloroglucinol yield of the order of 60%.

EXAMPLE 3

Hydrolysis of 1,3,5-triaminobenzene to phloroglucinol and its extraction with ethyl ether 2.2 g (18 mmol) of 1,3,5-triaminobenzene in 150 ml of a 2 N aqueous solution of hydrochloric acid are heated at 100° C. for 18 h. After cooling to ambient temperature, the solution is filtered. The aqueous phase is subsequently extracted with 3×40 ml of ethyl ether. The ethereal phases are dried over sodium sulfate, filtered and then evaporated.

The phloroglucinol obtained is subsequently recrystallized from 17 ml of water containing 15 mg of active carbon, giving 1.5 g of pure phloroglucinol.

EXAMPLE 4

Hydrolysis of 1,3,5-triaminobenzene to phloroglucinol and its purification with ethyl ether 5 g of 1,3,5-triaminobenzene in 300 ml of a 0.5 N aqueous solution of hydrochloric acid are heated at 120° C. for 15 hours. After cooling, the solution is concentrated until the phloroglucinol precipitates. The filtered precipitate is recrystallized from 40 ml of water with active carbon. The product obtained is subsequently taken up in a minimum of ethyl ether and heated for 15 minutes with active carbon. Evaporation gives 2.9 g of pure product.

EXAMPLE 5

Preparation of 1,3,5-triaminobenzene from 3,5-dichloroaniline, hydrolysis with hydrochloric acid of the 1,3,5-triaminobenzene to phloroglucinol.

A pressurized vessel is charged with 30 g (18.6 mmol) of 3.5-dichloroaniline and 1.8 g of copper iodide in 160 ml of 28% aqueous ammonia. The mixture is heated at 190° C. and under a pressure of 40 bars for 24 h. The contents of the vessel are poured into 200 ml of water and then the excess ammonia is removed. Then 56 g of 10 N hydrochloric acid are added and the mixture is heated at 110° C. for 20 h. Following filtration, the solution is cooled in an ice bath until the phloroglucinol precipitates. The precipitate obtained is subsequently recrystallized from 400 ml of a water-methanol (95 V–5 V) mixture. A second recrystallization from the same mixture gives 12.5 g of pure phloroglucinol.

EXAMPLE 6

Preparation of 1,3,5-triaminobenzene from 3,5-dichloroaniline; hydrolysis with sulfuric acid of the 1,3,5-triaminobenzene to phloroglucinol, and purification A pressurized vessel is charged with 30 g (18.6 mmol) of 3,5-dichloroaniline and 1.5 g of copper chloride in 160 ml of 28% aqueous ammonia. The mixture is heated at 190° C. and under a pressure of 37 bars for 24 hours. The contents of the vessel are poured into 200 ml of water and then the excess ammonia is removed. Then 37 g of 98% sulfuric acid are added and the mixture is heated at 110° C. for 20 hours. Following filtration, the solution is concentrated to a third and then cooled in an ice bath until the phloroglucinol precipitates. The precipitate obtained is subsequently recrystallized from 350 ml of a water-ethanol (93 V–7 V) mixture. A second recrystallization from water gives 13 g of pure phloroglucinol.

The invention claimed is:

1. A method of preparing 1,3,5-triaminobenzene, comprising a step a) of amination of a compound of formula (I):

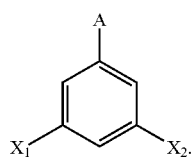

(I)

in which:
A represents a halogen atom or an NH2 group,
X1 and X2, which are identical or different, each represent a halogen atom,
said amination step being conducted in the presence of ammonia and a catalyst selected from the group consisting of copper salts, cupric and cuprous oxides and mixtures thereof, at a temperature ranging from 150° C. to 250° C. and at a pressure of greater than 35 bar.

2. The method of claim 1, wherein A represents a bromine atom, a chlorine atom or NH2 group.

3. The method of claim 1, wherein X1 and X2 are identical and each represent a chlorine atom or a bromine atom.

4. The method of claim 1, wherein the catalyst is selected from the group consisting of copper halides and cupric and cuprous oxides.

5. The method of claim 1, wherein the aqueous ammonia possesses a concentration of 20% to 30%.

6. The method of claim 1, further comprising the steps of:
b) hydrolysis of the 1,3,5-triaminobenzene obtained at the end of the amination step in the presence of hydrochloric acid or of sulfuric acid at a temperature greater than 90° C., for a time of 6 to 24 h, to give a hydrolysate containing phloroglucinol,
c) optionally filtration at ambient temperature of the hydrolysate obtained in step b),
d) extraction of phloroglucinol from the hydrolysate obtained in step b) or from the filtrate obtained in step c), using ethyl ether or an ester-based solvent.

7. The method of claim 1, further comprising the steps of:
b) hydrolysis of the 1,3,5-triaminobenzene obtained at the end of the amination step at a temperature greater than 90° C., for a time of 6 to 24 h, to give a hydrolysate containing phloroglucinol, wherein the hydrolysis is conducted in the presence of hydrochloric acid at a concentration of 20% to 40%
c) optionally filtration at ambient temperature of the hydrolysate obtained in step b),
d) extraction of phloroglucinol from the hydrolysate obtained in step b) or from the filtrate obtained in step c), using ethyl ether or an ester-based solvent.

8. The method of claim 1, further comprising the steps of:
b) hydrolysis of the 1,3,5-triaminobenzene obtained at the end of the amination step at a temperature greater than 90° C., for a time of 6 to 24 h, to give a hydrolysate containing phloroglucinol, wherein the hydrolysis is conducted in the presence of sulfuric acid at a concentration of 10% V to 100% V,
c) optionally filtration at ambient temperature of the hydrolysate obtained in step b),
d) extraction of phloroglucinol from the hydrolysate obtained in step b) or from the filtrate obtained in step c), using ethyl ether or an ester-based solvent.

9. The method of claim 1, further comprising the steps of:
b) hydrolysis of the 1,3,5-triaminobenzene obtained at the end of the amination step in the presence of hydrochloric acid or of sulfuric acid at a temperature greater than 90° C., for a time of 6 to 24 h, to give a hydrolysate containing phloroglucinol,
c) optionally filtration at ambient temperature of the hydrolysate obtained in step b),
d) extraction of phloroglucinol from the hydrolysate obtained in step b) or from the filtrate obtained in step c), using ethyl ether or an ester-based solvent,
e1) recrystallization of the phloroglucinol obtained in step c) or step d) from water containing active carbon, to give a high-purity phloroglucinol.

10. The method of claim 1, further comprising the steps of:
b) hydrolysis of the 1,3,5-triaminobenzene obtained at the end of the amination step in the presence of hydrochloric acid or of sulfuric acid at a temperature greater than 90° C., for a time of 6 to 24 h, to give a hydrolysate containing phloroglucinol,
c) optionally filtration at ambient temperature of the hydrolysate obtained in step b), d) extraction of phloroglucinol from the hydrolysate obtained in step b) or from the filtrate obtained in step c), using ethyl ether or an ester-based solvent, e2) concentration of the hydrolysate obtained in step c) or of the phloroglucinol solution obtained in step d) until phloroglucinol precipitates, f2) filtration of the precipitate obtained in step e2), g2) recrystallization of the phloroglucinol obtained in step f2) from water containing active carbon, h2) takeup of the recrystallized phloroglucinol obtained in step g2) in ethyl ether containing active carbon, to give a phloroglucinol solution, i2) evaporation of the phloroglucinol solution obtained in step h2), to give a high-purity phloroglucinol.

11. The method of claim 1 further comprising the step of using the 1,3,5-triamiobenzene to produce phloroglucinol.

12. The method of claim 2 wherein A represents a chlorine atom or a $NH_2$ group.

13. The method of claim 12 wherein A represents a chlorine atom.

14. The method of claim 3 wherein $X_1$ and $X_2$ are identical and each represent a chlorine atom.

15. The method of claim 4 wherein said catalyst is copper iodide.

16. The method of claim 5 wherein the aqueous ammonia possesses a concentration of 28%.

17. The method of claim 6 wherein the hydrolysis of the 1,3,5-triaminobenzene in step b) is at a temperature of from 100 to 120° C.

18. The method of claim 6 wherein the extraction of phloroglucinol from the hydrolysate obtained in step b) or from the filtrate obtained in step c) uses ethyl benzoate, ethyl acetate, isopropyl acetate or n-butyl acetate.

19. The method of claim 7 wherein the hydrolysis of the 1,3,5-triaminobenzene in step b) is at a temperature of from 100 to 120° C.

20. The method of claim 7 wherein the hydrolysis is conducted in the presence of hydrochloric acid at a concentration of 37%.

21. The method of claim 7 wherein the extraction of phloroglucinol from the hydrolysate obtained in step b) or from the filtrate obtained in step c) uses ethyl benzoate, ethyl acetate, isopropyl acetate or n-butyl acetate.

22. The method of claim 8 wherein the hydrolysis of the 1,3,5-triaminobenzene in step b) is at a temperature of from 100 to 120° C.

23. The method of claim 8 wherein the hydrolysis of the 1,3,5-triaminobenzene is conducted in the presence of sulfuric acid at the concentration of from 50% V to 98% V.

24. The method of claim 8 wherein the extraction of phloroglucinol from the hydrolysate obtained in step b) or from the filtrate obtained in step c) uses ethyl benzoate, ethyl acetate, isopropyl acetate or n-butyl acetate.

25. The method of claim 9 wherein the hydrolysis of the 1,3,5-triaminobenzene in step b) is at a temperature of from 100 to 120° C.

26. The method of claim 9 wherein the extraction of phloroglucinol from the hydrolysate obtained in step b) or from the filtrate obtained in step c) uses ethyl benzoate, ethyl acetate, isopropyl acetate or n-butyl acetate.

27. The method of claim 10 wherein the hydrolysis of the 1,3,5-triaminobenzene in step b) is at a temperature of from 100 to 120° C.

28. The method of claim 10 wherein the extraction of phloroglucinol from the hydrolysate obtained in step b) or from the filtrate obtained in step c) uses ethyl benzoate, ethyl acetate, isopropyl acetate or n-butyl acetate.

* * * * *